United States Patent [19]

Zwart, Jr.

[11] Patent Number: 4,686,078

[45] Date of Patent: Aug. 11, 1987

[54] METHOD AND APPARATUS FOR DISPLACING A REACTOR WELD SCANNER ASSEMBLY BY VARIABLE BUOYANCY

[75] Inventor: Bernardus M. Zwart, Jr., New Canaan, Conn.

[73] Assignee: Nuclear Energy Services, Inc., Danbury, Conn.

[21] Appl. No.: 721,180

[22] Filed: Apr. 8, 1985

[51] Int. Cl.⁴ .................... G21C 17/00; G01N 29/04; G01N 9/24
[52] U.S. Cl. ...................................... 376/249; 73/623; 73/634; 73/637
[58] Field of Search .................. 376/249; 73/622, 623, 73/638, 640, 634, 637

[56] References Cited

U.S. PATENT DOCUMENTS

| | | |
|---|---|---|
| 3,780,571 | 12/1973 | Wiesner ............................... 376/249 |
| 3,901,073 | 8/1975 | Dent et al. ........................... 376/249 |
| 3,943,756 | 3/1976 | Aubert et al. ....................... 376/249 |
| 4,336,103 | 6/1982 | Katscher et al. .................... 376/245 |
| 4,372,161 | 2/1983 | de Buda et al. .................... 376/249 |
| 4,470,952 | 9/1984 | Vassalotti ............................ 376/249 |

Primary Examiner—Salvatore Cangialosi
Attorney, Agent, or Firm—Charles J. Brown

[57] ABSTRACT

A method, and an apparatus for carrying out the method, for displacing a weld scanner in and out of a horizontal reactor vessel nozzle submerged in a water pool characterized by buoyancy chambers into which water and air may be introduced by remote control to move the scanner and an associated telescopic boom, column and spider into position relative to the reactor vessel.

18 Claims, 14 Drawing Figures

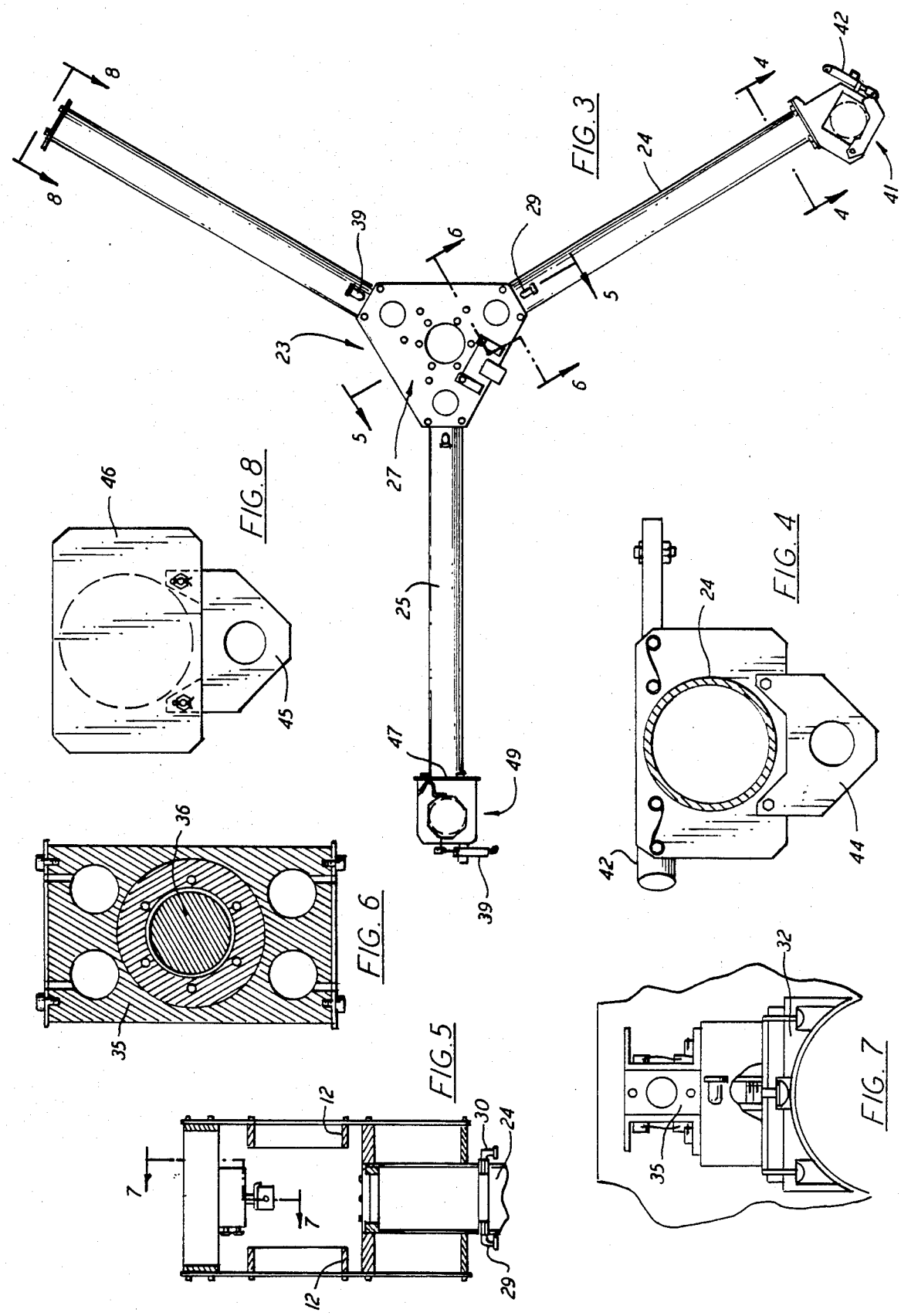

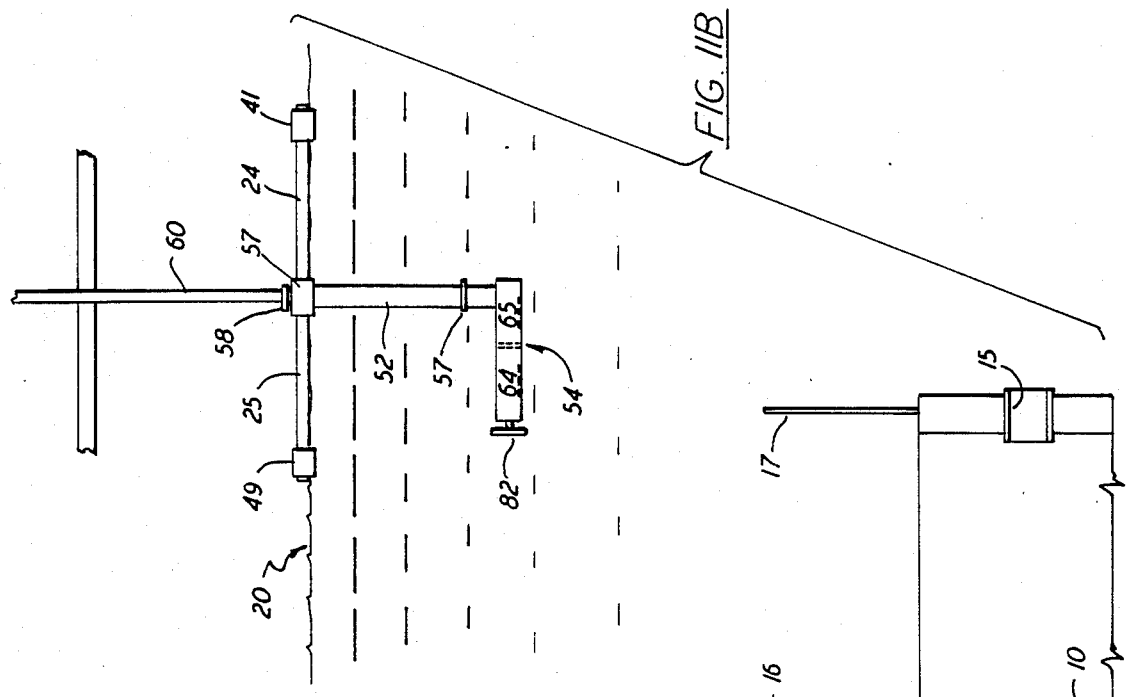
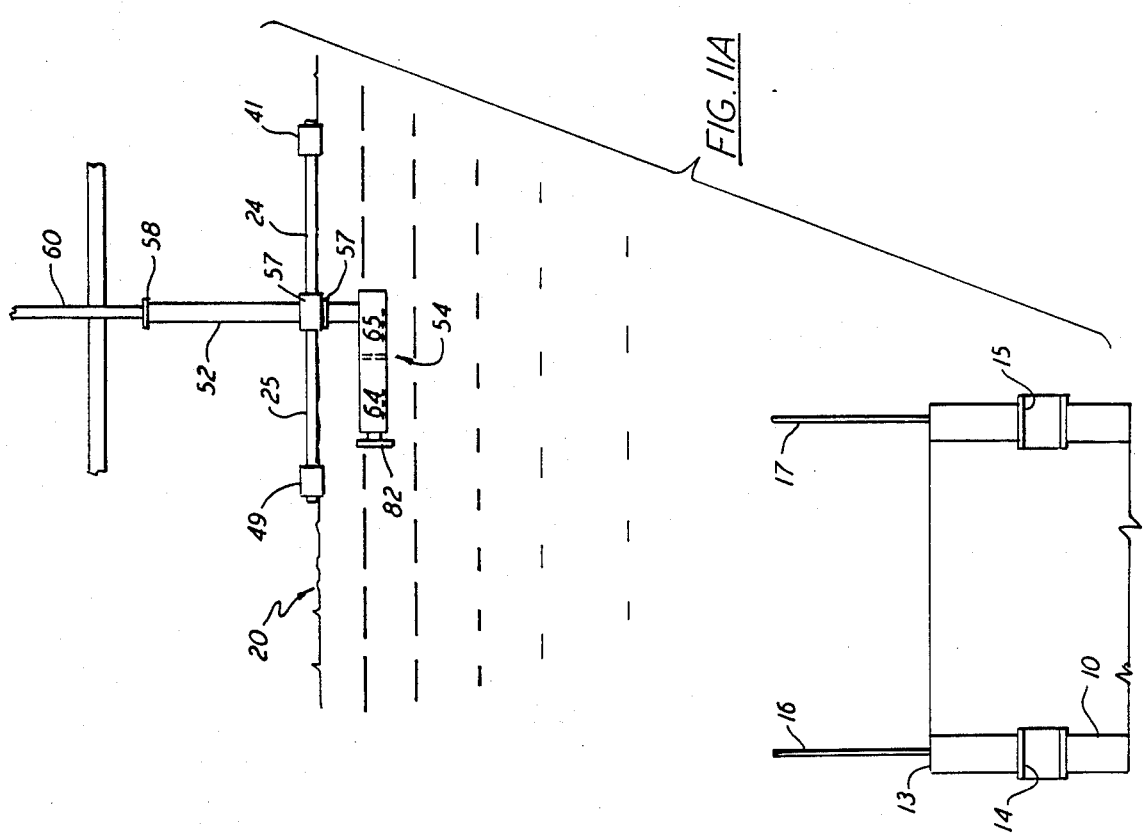

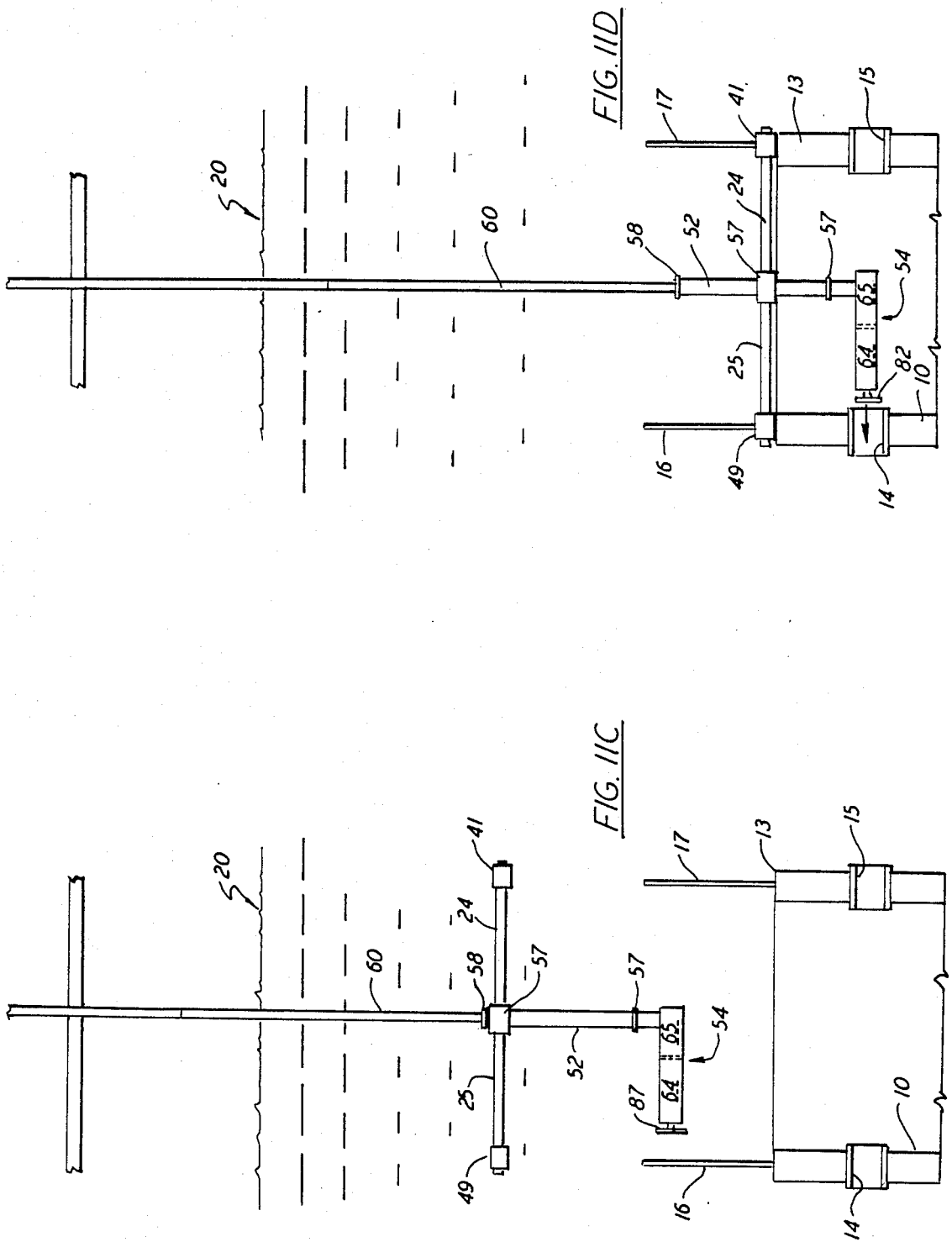

METHOD AND APPARATUS FOR DISPLACING A REACTOR WELD SCANNER ASSEMBLY BY VARIABLE BUOYANCY

BACKGROUND OF THE INVENTION

Nuclear reactor ultrasonic inspection devices have long been available for scanning welds when a reactor is shut down for refuelling and its open reactor vessel is submerged in a water pool. Such devices typically include a spider assembly having legs spanning the reactor vessel flange at its open upper end, a telescopic vertical column mounted in the hub of the spider coaxial with the vessel, and a telescopic horizontal boom at the lower end of the column carrying the scanner. U.S. Pat. No. 3,780,571 is typical of the disclosures of such devices.

It is characteristic of prior art inspection apparatus that they involve complicated telescopic and rotational drives often with pulley and cable systems, all of relatively high cost and substantial weight. It is the principal purpose of the present invention to provide a method and apparatus for displacing a reactor weld scanner into and out of position by a system which is inexpensive and which can be assembled at the site with lightweight individual parts transportable by one man.

SUMMARY OF THE INVENTION

The invention provides a method of displacing a weld scanner in and out of a horizontal reactor vessel nozzle, wherein vertical guide studs extend upwardly from an upper circular vessel flange with the studs and vessel submerged in a water pool. The scanner is mounted on a horizontal positively driven telescopic boom to which a vertical column is attached which is slideable between stop limits within a hub of a spider having legs adapted to span the flange with clamps on the outer ends of at least two legs adapted to slide on and grip two of the studs. Any or all of the boom and column and spider legs defines a buoyancy chamber into which air and water may be introduced. The method comprises the steps of first introducing air into the buoyancy chamber. The scanner-boom-columnmn-spider assembly is then floated in the pool with the upper end of the column extending above and the scanner and boom extending below the water surface. Some water is then introduced into the chamber to cause the scanner-boom-column to sink relative to the spider until the column is stopped at its lower limit in the hub. Positioning rod means are then affixed coaxially to the upper end of the column. More water is then introduced into the buoyancy chamber to sink the scanner-boom-column-spider assembly at substantially neutral buoyancy with the rod means projecting at its upper end above the pool surface. The rod means are then manipulated and then more water is introduced into the buoyancy chamber so that the leg clamps are lowered about the studs and the spider legs descend onto the vessel flange. The clamps are then closed to fix the spider relative to the vessel. The rod means are next moved vertically and rotated to bring the scanner to a level coaxial with the nozzle. The telescopic boom is then positively extended to enable inspection by the scanner in the nozzle. After inspection the boom is positively retracted and the spider clamps are opened. Air is then introduced into the chamber until the entire assembly is buoyant. The rod means are manipulated as the assembly lifts upwardly off the studs and to the surface and then the rod means are detached.

In a preferred form of the method the spider has three legs, two of which have clamps slideable on two studs, each of the three legs having a buoyancy chamber. Each of the boom and column may also define a buoyancy chamber. The column may be rotatable on the hub and adapted to be braked with respect to the hub. After retraction the boom may be rotated by the rod means to be under one of the spider legs. After the boom is retracted and before the clamps are opened air may be introduced into the spider legs chambers to render them positively buoyant while the other chambers are still negatively buoyant. The water introduced into the buoyancy chambers may be maintained separate from the pool water. The boom may be provided with two fore and aft buoyancy chambers.

In combination with a weld scanner mounted on a positively driven telescopic boom to which a perpendicular column is attached, the invention also provides apparatus for buoyantly displacing the scanner in and out of a horizontal reactor vessel nozzle wherein vertical guide studs extend upwardly from an upper circular vessel flange with the studs and vessel submerged in a water pool. The apparatus of the invention comprises a spider having legs adapted to span the flange. A central hub is provided in the spider in which the column is slideable. Stop means are included for limiting the slideable movement of the column in the hub. Clamps operable by remote control are included on the outer ends of at least two legs adapted to slide and grip two of the studs. At least one of the boom and column and spider legs defines a buoyancy chamber. Means operable by remote control are included for introducing air into and releasing it from the chambers. Means operable by remote control are also included for introducing water into and draining it from the chambers. Positioning rod means are provided coaxially attachable to the column remote from the boom for manipulating the scanner-boom-column-spider assembly when submerged. The weight of this apparatus is such that it is buoyant in water when air is introduced into the chambers.

In a preferred form of the apparatus two guide studs extend from the flange approximately 120 degrees apart and the spider has three substantially equally spaced legs with clamps included on two of the legs. Each of the boom and column and spider legs may define a buoyancy chamber and the boom may define two fore and aft chambers. The water supply for all of the chambers may be separate from the pool water. Braking means operable by remote control may be provided for controlling axial and rotational displacement of the column in the spider hub.

BRIEF DESCRIPTION OF THE DRAWINGS

FIG. 3 is an enlarged top plan view of the spider assembly of the invention;

FIG. 4 is a section taken along the line 4—4 of FIG. 3;

FIG. 5 is a section of the spider hub taken along the line 5—5 of FIG. 3;

FIG. 6 is a section of one spider leg taken along the line 6—6 of FIG. 3;

FIG. 7 is a section taken along the line 7—7 of FIG. 5;

FIG. 8 is an end view of one of the spider legs taken along the line 8—8 of FIG. 3;

FIGS. 11A through 11D are schematic illustrations of four sequential steps in the practice of the method of the invention with reference to the apparatus of FIGS. 1 to 10.

DESCRIPTION OF PREFERRED EMBODIMENT

Figure 2:
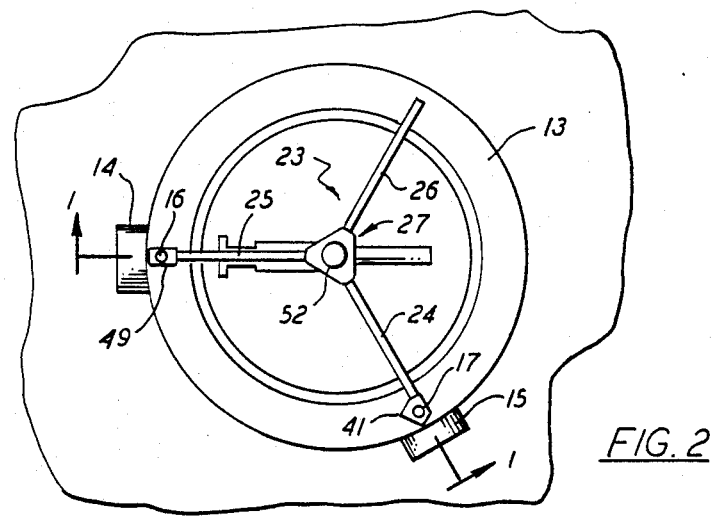
FIG. 2 is a sectional plan view taken along the line 2—2 of FIG. 1.
Figure 1:
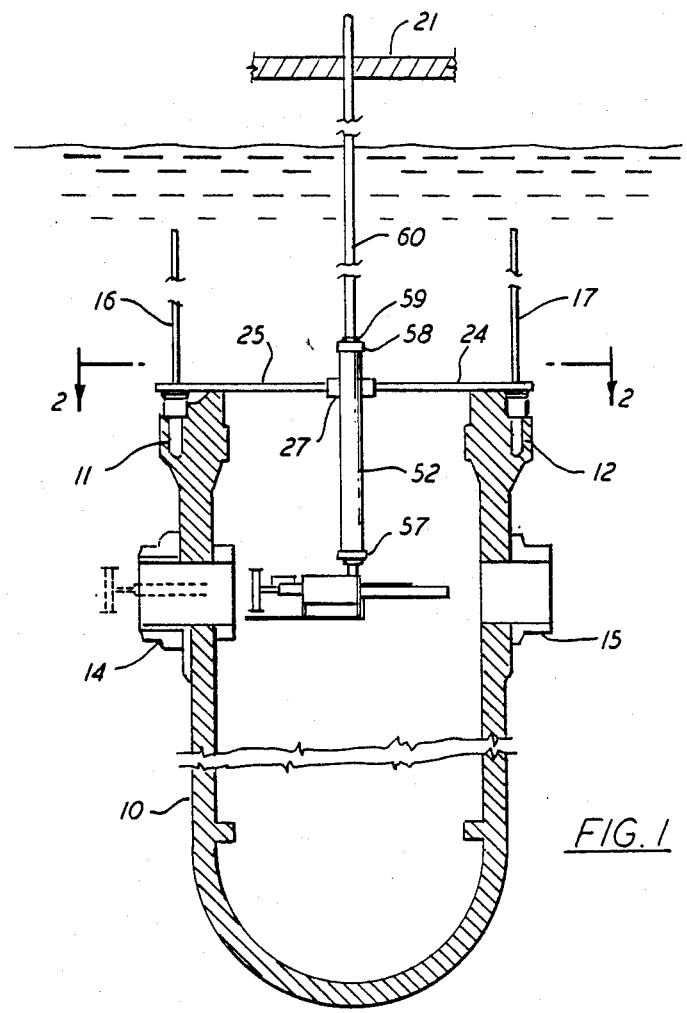
FIG. 1 is a side elevation in section and partly broken away of a PWR reactor vessel with its head removed and a scanner assembly according to the invention installed in place, the section being taken along the angled section line 1—1 of FIG. 2.

Referring first to FIGS. 1 and 2, the reactor vessel shell 10 is shown with its head removed from a circular flange 13. A horizontal outlet nozzle 14 extends through the shell 10 and approximately 120 degrees away from it is a similarly positioned horizontal inlet nozzle 15. Guide studs 16 and 17 are shown screwed in two of many equally spaced stud holes (for example 52 in number) in the flange 13. It will be evident from FIG. 2 that the guide stud 17 and inlet nozzle 15 have been rotated 60 degrees from their true plane so as to be visible in section in FIG. 1 and hence the section line of 1—1 in FIG. 2 is angled.

The method and apparatus of the invention are applicable to ultrasonic inspection of the welds within the outlet and inlet nozzles 14 and 15 respectively. The vertical guide studs 16 and 17 extending upwardly from the upper circular vessel flange 13 are submerged in a water pool having a surface 20 many feet above the upper ends of the guide studs 16 and 17. Well above the water pool surface 20 is a refuelling bridge structure suggested schematically at 21 in FIG. 1 from which personnel may work during the assembly and operation of the apparatus of the invention.

Referring now to FIG. 3 and to FIGS. 4 to 8 which are sections thereof, a spider assembly designated generally by 23 is shown to include three basically tubular legs 24, 25 and 26 spaced approximately 120 degrees apart. A hub assembly 27 joins the converging ends of the legs 24, 25 and 26 in position such that the outer ends of the legs extend radially outwardly a distance sufficient to span the flange 13 of the reactor vessel. As shown in FIG. 5, the hub assembly includes a pair of bushings 12 coaxial with the center of the spider assembly 23. The tubular leg 24 is shown in FIG. 5 projecting from the hub assembly and is equipped with an air tap 29 and a water tap 30 communicating with its hollow interior. The interior of the leg 24 thus forms a buoyancy chamber. Referring to FIG. 7, a brake shoe 32 operable by a pneumatic cylinder assembly 33 is provided within the hub assembly 27 to operate between the bushings 12. An inner leg mounting block 35 is shown in section in FIG. 6 to illustrate the manner in which each of the legs is affixed to the hub assembly 27 of the spider assembly 23. Closure means 36 shown in FIG. 6 constitutes the end wall of the buoyancy chamber defined by the leg 24.

Air taps 38 and 39 on the legs 25 and 26 respectively are similar to the air tap 29 on the leg 24. Associated water taps not visible in the drawings are provided opposite the air taps 38 and 39 for the legs 25 and 26 just as the water tap 30 is located opposite the air tap 29 for the leg 24. Each of the tubular legs 25 and 26 defines its own buoyancy chamber in a manner similar to the leg 24.

As shown in FIG. 3, at the outer end of the leg 24 is an articulated clamp 41 operated by a pneumatic cylinder 42. As will be clear from the following description the clamp 41 is adapted to slide on and grip the guide stud 17. As shown in FIG. 4 an end plate of the leg 40 to which the clamp 41 is attached includes a flange spacer 44 which serves as a foot for resting on the reactor flange 13. FIG. 8 illustrates a similar flange spacer 45 affixed to an end plate 46 at the end of the leg 26. A third flange spacer not shown in the drawings is provided on an end plate 47 at the outer end of the third leg 25 of the spider assembly. As shown in FIG. 3 there is mounted to the end plate 47 a clamp 49 operable by a pneumatic air cylinder 50. The clamp 49 is adapted to slide on and grip the guide stud 16 extending upwardly from the flange 13 of the reactor vessel. Each of the air cylinders 33 for the brake shoe 32, and the air cylinders 42 for the clamp 41 and the air cylinder 50 for the clamp 49 is operated by remote control through pneumatic lines which are not shown in the drawings but which extend to an appropriate control station on the refuelling bridge 21 above the surface 20 of the water pool.

Figure 9:
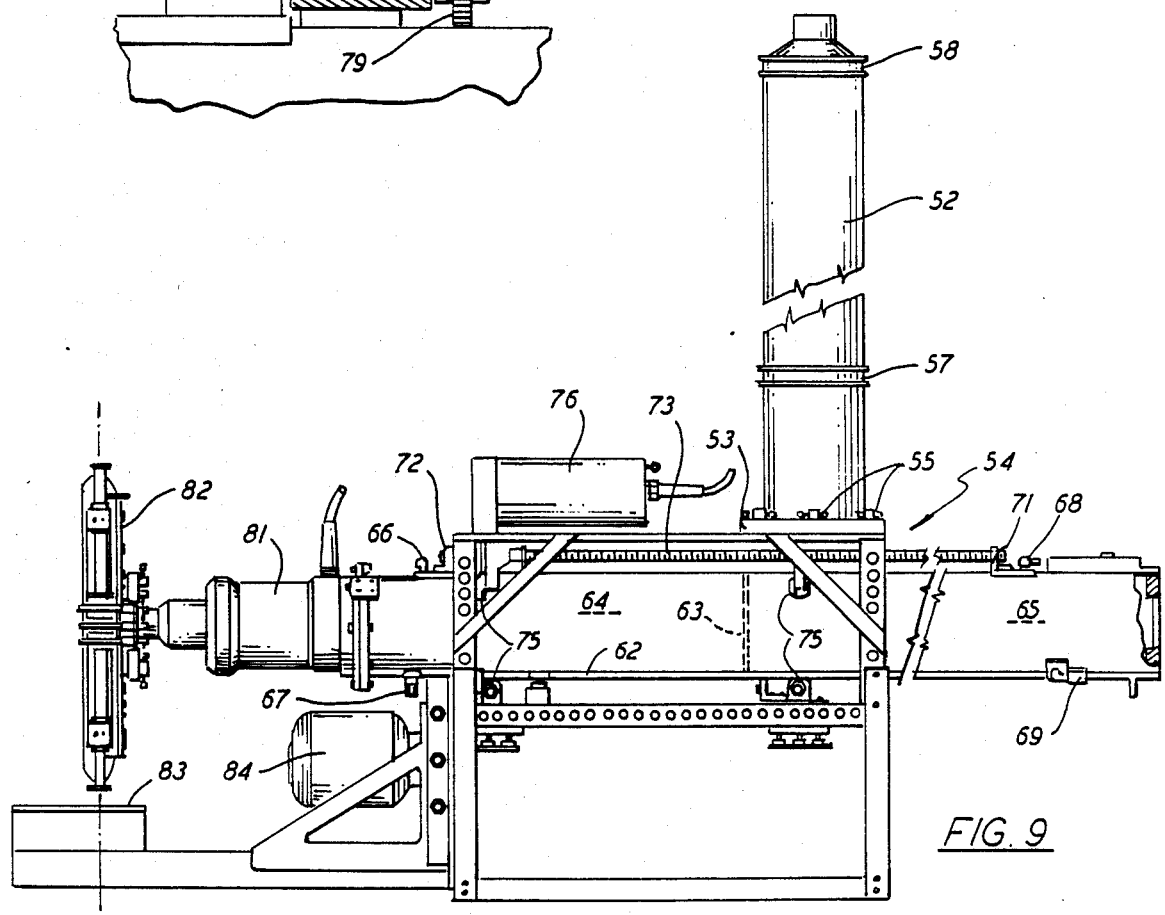
FIG. 9 is an enlarged elevation partly broken away of the vertical column and telescopic boom of the invention.

The bushings 12 of the hub assembly 27 are designed to fit around a vertical column 52 shown in FIG. 9. The total length of the vertical column is approximately six feet. The lower end of the column 52 is attached to a frame 53 of a boom assembly 54 by the use of captive screws 55. The column 52 is provided with a circumferential lower stop 57 which is permanently in place and an upper circumferential stop 58 which is positioned by hose clamps after the vertical column 52 is placed within the bushings 12 of the hub assembly 57. At the extreme upper end of the column 52 above the stop 58 is a socket 59 for receiving one or more positioning rods 60 coaxially attachable to the column remote from the boom assembly 54. The upper end of the positioning rod 60 extends above and adjacent the refuelling bridge structure for appropriate manipulation by the operator. The vertical column 52 is tubular and hollow and defines its own buoyancy chamber provided with air and water taps and appropriate hoses (not shown in the drawings) similar to those provided for the legs 24, 25 and 26 of the spider assembly.

The boom assembly 54 includes a boom tube 62 which is hollow, sealed off at both ends and divided by a central bulkhead 63 into a fore buoyancy chamber 64 and an aft buoyancy chamber 65. The fore buoyancy chamber 64 is equipped with an air tap 66 and a water tap 67. The aft buoyancy chamber is equipped with an air tap 68 and a water tap 69. The taps and associated air hoses are also similar to those provided for the spider legs.

Figure 10:
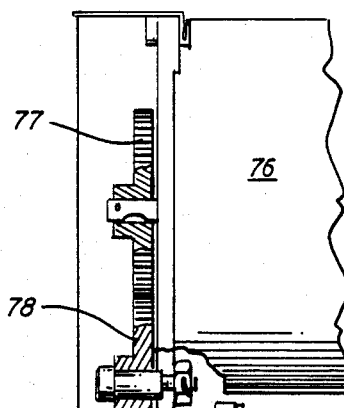
FIG. 10 is an enlarged fragmentary view of the telescopic drive of the boom of FIG. 9.

Fixed to the boom tube 62 by brackets 71 and 72 is a lead screw 73. The boom tube 62 and its lead screw 73 translate back and forth horizontally in engagement with various rollers 75. This displacement is effected by an electric motor 76 on the frame 53 which, as shown in detail in FIG. 10, drives gears 77, 78 and 79 to move the boom tube 62 telescopically in relation to the boom frame 53.

Projecting forwardly from the end of the boom tube 62 is an electric rotator 81 which turns an ultrasonic scanner device 82. A target 83 for calibration of the scanner device 82 is fixed on the frame 53 of the boom assembly. Also affixed on the frame 53 of the boom assembly is a headlamp 84 for use in the event a television monitor is also provided.

Suitable pneumatic and hydraulic lines and electrical conductors are provided to the various air and water taps, motors and lights described above. All of these service lines are routed upwardly to the previously mentioned control station on the refuelling bridge 21. The stroke of the scanner 82 on the telescopic boom assembly 54 is almost four feet so that the scanner can move from the retracted position shown in solid lines in FIG. 1 to the dotted line position well within the outlet nozzle 14.

The method of the invention with reference to the foregoing apparatus will now be described in relation to FIGS. 11A through 11D. It is to be emphasized that FIGS. 11A-D are wholly schematic and are included solely for purposes of illustrating the sequence of steps carried out during the operation of the apparatus described above.

Referring first to FIG. 11 1A, the two spaced vertical guide studs 16 and 17 extend upwardly from the upper circular vessel flange 13, approximately 120 degrees apart with the studs and vessel 10 submerged in a water pool indicated by the surface 20. The scanner 82 is mounted on the horizontal positively driven telescopic boom assembly 54 to which the vertical column 52 is attached. The column is slideable between stop limits 57 and 58 and rotatable within and can be braked with respect to a hub assembly 27 of a spider having three substantially equally spaced legs (24 and 25 of which are shown) adapted to span the flange 13. Clamps 41 and 49 are on the outer ends of the legs 24 and 25. Each of the column 52 and spider legs defines one buoyancy chamber and the boom assembly 54 defines fore and aft buoyancy chambers 64 and 65 into which air and water may be introduced.

The method provides for introducing air into each of the various buoyancy chambers in the initial position of the apparatus shown in FIG. 11A. Next the scanner-boom-column-spider assembly is floated in the water pool with the upper end of the column 52 extending above and the scanner 82 and boom assembly 54 extending below the water surface 20. Some water, separate from the pool water, is then introduced into the aft chamber 65 of the boom assembly 54. The brake shoe 32 operating on the column 52 is then turned off and on in short bursts to allow the column 52 to slide gently down through the spider hub assembly 27 until the stop 58 at the upper end of the column 52 is against the spider hub 27 in the position shown in FIG. 11B.

A ten-foot section of positioning rod 60 is then attached to the upper end of the column 52 by snapping it into the socket 59. Water is then introduced into all buoyancy chambers until the entire assembly achieves neutral buoyancy. An operator on the refuelling bridge 21 then pushes downwardly on the positioning rod 60, and adds another ten-foot section of positioning rod if necessary. As the assembly is pushed downward it will become more buoyant due to the buoyancy of the upper column section and this is to be counteracted by the introduction of additional water into the buoyancy chambers. The operator then manipulates the rod means and introduces more water (separate from the pool water) into all of the buoyancy chambers so that the two leg clamps 41 and 49 are lowered about the stud guides 17 and 16 respectively and all three spider legs 24, 25 and 26 descend onto the vessel flange 13. The two clamps 41 and 49 are then closed pneumatically to fix the spider relative to the vessel.

Next the positioning rod 60 is moved vertically and rotated to bring the scanner to a level coaxial with the nozzle. The boom assembly is then telescopically extended to enable inspection by the scanner within the nozzle and thereafter is retracted.

After the inspection, air is introduced into the spider leg chambers to render them positively buoyant while the other chambers are still negatively buoyant. The boom assembly 54 is next rotated by the positioning rod 60 so that it is under the spider leg 26 which does not have a clamp. Clamps 41 and 49 are then opened. Air is introduced first into the boom fore chamber 64 and then into the boom aft chamber 65 so that the entire assembly is buoyant. The rod 60 is then manipulated and eventually detached as the assembly floats upwardly off the studs 16 and 17 to the surface. The braking of the hub 58 on the column 52 is ceased to cause the scanner-boom-column to rise relative to the spider until the column is stopped at its upper limit in the hub. This final position is once again as shown in FIG. 11A.

I claim:

1. A method of displacing a weld scanner in and out of a horizontal reactor vessel nozzle, wherein vertical guide studs extend upwardly from an upper circular vessel flange with the studs and vessel submerged in a water pool, the scanner being mounted on a horizontal positively driven telescopic boom to which a vertical column is attached which is slideable between stop limits within a hub of a spider having legs adapted to span the flange with clamps on the outer ends of at least two legs adapted to slide on and grip two of said studs, at least one of the boom and column and spider legs defining a buoyancy chamber into which air and water may be introduced, comprising the steps of
   (a) introducing air into the buoyancy chamber,
   (b) floating the scanner-boom-column-spider assembly in the pool with the upper end of the column extending above and the scanner and boom extending below the water surface,
   (c) introducing some water into the chamber to cause the scanner-boom-column to sink relative to the spider until the column is stopped at its lower limit in the hub,
   (d) affixing positioning rod means coaxial by to the upper end of the column,
   (e) introducing more water into the chamber to sink the scanner-boom-column-spider assembly at substantially neutral buoyancy with the rod means projecting at its upper end above the pool surface,
   (f) manipulating the rod means and introducing more water into the buoyancy chamber so that the leg clamps are lowered about the studs and the spider legs descend onto the vessel flange,
   (g) closing the clamps to fix the spider relative to the vessel,
   (h) moving the rod means vertically and rotating it to bring the scanner to a level coaxial with the nozzle,
   (i) positively extending the telescopic boom to enable inspection by the scanner in the nozzle,
   (j) positively retracting the boom after inspection,
   (k) opening the spider clamps,
   (l) introducing air into the chamber until the entire assembly is buoyant, and
   (m) manipulating and then detaching the rod means as the assembly floats upwardly off the studs and to the surface.

2. A method according to claim 1 wherein the spider has three legs two of which have two clamps slideable on two studs, each of the three legs having a buoyancy chamber.

3. A method according to claim 2 wherein after retraction the boom is rotated by the rod means to be under one of the spider legs.

4. A method according to claim 1 wherein each of the boom and column and spider legs define buoyancy chambers.

5. A method according to claim 1 wherein the boom is provided with two fore and aft buoyancy chambers.

6. A method according to claim 1 wherein the column is rotatable in the hub.

7. A method according to claim 1 wherein the column can be braked in the hub.

8. A method according to claim 1 wherein after the boom is retracted and before the clamps are opened air is introduced into the spider leg chambers to render them positively buoyant while the other chambers are still negatively buoyant.

9. A method according to claim 1 wherein the water introduced into the buoyancy chambers is maintained separate from the pool water.

10. A method of displacing a weld scanner in and out of a horizontal reactor vessel nozzle, wherein two spaced vertical guide studs extend upwardly from an upper circular vessel flange approximately 120 degrees apart with the studs and vessel submerged in a water pool, the scanner being mounted on a horizontal positively driven telescopic boom to which a vertical column is attached which is slideable between stop limits and rotatable within and can be braked with respect to a hub of a spider having three equally spaced legs adapted to span the flange with clamps on the outer ends of two of the legs adapted to slide on and grip two of the studs, each of the columns and spider legs defining one buoyancy chamber and the boom defining two fore and aft buoyancy chambers into which air and water may be introduced, comprising the steps of
    (a) introducing air into each of the buoyancy chambers,
    (b) floating the scanner-boom-column-spider assembly in the pool with the upper end of the column extending above and the scanner and boom extending below the water surface,
    (c) introducing some water separate from the pool water into the boom chamber while controlling the braking of the hub and column to cause the scanner-boom-column to sink relative to the spider until the column is stopped at its lower limit in the hub,
    (d) braking the hub to the column,
    (e) affixing positioning rod means coaxially to the upper end of the column,
    (f) introducing more water separate from the pool water into all of the buoyancy chambers to sink the scanner-boom-column-spider assembly at substantially neutral buoyancy with the rod means projecting at its upper end above the pool surface,
    (g) manipulating the rod means and introducing more water separate from the pool water into all of the buoyancy chambers so that the two leg clamps are lowered about two of the studs and all three spider legs descend onto the vessel flange,
    (h) closing the two clamps to fix the spider relative to the vessel,
    (i) moving the rod means vertically and rotating it to bring the scanner to a level coaxial with the nozzle,
    (j) positively extending the telescopic boom to enable inspection by the scanner in the nozzle,
    (k) positively retracting the boom after inspection,
    (l) introducing air into the spider leg chambers to render them positively buoyant while the other chambers are still negatively buoyant,
    (m) rotating the boom by the rod means so that it is under the spider leg without a clamp,
    (n) opening the spider clamps,
    (o) introducing air first into the boom fore chamber and then into the boom aft chamber so that the entire assembly is buoyant,
    (p) manipulating and then detaching the rod means as the assembly floats upwardly off the studs and to the surface. the assembly floats upwardly off the studs and to the surface.
    (q) introducing air into all of the chambers when the assembly is on the pool surface.
    (r) ceasing the braking of the hub on the column to cause the scanner-boom-column to rise relative to the spider until the column is stopped at its upper limit in the hub, and
    (s) removing the assembly from the pool.

11. In combination with a weld scanner mounted on a positively driven telescopic boom to which a perpendicular column is attached, apparatus for buoyantly displacing the scanner in and out of a horizontal reactor vessel nozzle wherein vertical guide studs extend upwardly from an upper circular vessel flange with the studs and vessel submerged in a water pool, comprising
    (a) a spider having legs adapted to span the flange,
    (b) a central hub in the spider in which the column is slideable,
    (c) stop means for limiting the slideable movement of the column in the hub,
    (d) clamps operable by remote control on the outer ends of at least two legs adapted to slide on and grip two of said studs,
    (e) at least one of the boom and column and spider legs defining a buoyancy chamber,
    (f) means operable by remote control for introducing air into and releasing it from said chamber,
    (g) means operable by remote control for introducing water into and draining it from said chamber, and
    (h) positioning rod means coaxially attachable to the column remote from the boom for manipulating the scanner-boom-column-spider assembly when submerged,
    (i) the weight of the apparatus being such that it is buoyant in water when air is introduced into said chamber.

12. Apparatus according to claim 11 wherein two guide studs extend from the flange approximately 120 degrees apart.

13. Apparatus according to claim 12 wherein the spider has three substantially equally spaced legs and clamps are included on two of said legs.

14. Apparatus according to claim 11 wherein each of the boom and column and spider legs defines a buoyancy chamber.

15. Apparatus according to claim 11 wherein the boom defines two fore and aft chambers.

16. Apparatus according to claim 11 wherein the water supply for the chambers is separate from the pool water.

17. Apparatus according to claim 11 wherein braking means operable by remote control are provided for controlling axial and rotational displacement of the column in the spider hub.

18. In combination with an ultrasonic weld scanner mounted on a positively driven telescopic boom operable by remote control to which a perpendicular column is attached, apparatus for buoyantly displacing the scanner in and out of a horizontal reactor vessel nozzle, wherein two vertical guide studs extend upwardly from an upper circular vessel flange approximately 120 degrees apart with the studs and vessel submerged in a water pool, comprising (a) a spider having three substantially equally spaced legs adapted to span the flange,
(b) a central hub in the spider in which the column is slideable,
(c) braking means operable by remote control for controlling axial and rotational displacement of the column in the spider hub,
(d) clamps operable by remote control on the outer ends of two of said legs adapted to slide on and grip two of said studs,
(e) each of the columns and spider legs defining a single buoyancy chamber and the boom defining two fore and aft buoyancy chambers,
(f) means operable by remote control for introducing water into and releasing it from said chambers,
(g) means operable by remote control for introducing water into and releasing it from said chambers,
(h) said introduced water being separate from the pool water, and
(i) positioning rod means coaxially attachable to the column remote from the boom for manipulating the scanner-boom-column-spider assembly when submerged,
(j) the weight of the apparatus being such that it is buoyant in water when air is introduced into all of said chambers.

* * * * *